(12) United States Patent
Meetz et al.

(10) Patent No.: US 10,045,755 B2
(45) Date of Patent: Aug. 14, 2018

(54) PERFUSION IMAGING SYSTEM WITH A PATIENT SPECIFIC PERFUSION MODEL

(71) Applicant: KONINKLIJKE PHILIPS N.V., Eindhoven (NL)

(72) Inventors: Kirsten Meetz, Hamburg (DE); Ingwer Carlsen, Hamburg (DE); Heinrich Schulz, Hamburg (DE); Rafael Wiemker, Kisdorf (DE); Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 825 days.

(21) Appl. No.: 14/284,429

(22) Filed: May 22, 2014

(65) Prior Publication Data

US 2014/0257094 A1 Sep. 11, 2014

Related U.S. Application Data

(63) Continuation-in-part of application No. 12/920,483, filed as application No. PCT/IB2009/050757 on Feb. 25, 2009, now abandoned.

(60) Provisional application No. 61/037,010, filed on Mar. 17, 2008.

(51) Int. Cl.
*A61B 6/00* (2006.01)
*A61B 6/03* (2006.01)

(52) U.S. Cl.
CPC ............ *A61B 6/5217* (2013.01); *A61B 6/032* (2013.01); *A61B 6/461* (2013.01); *A61B 6/467* (2013.01); *A61B 6/501* (2013.01); *A61B 6/503* (2013.01); *A61B 6/504* (2013.01)

(58) Field of Classification Search
CPC ......... A61B 6/032; A61B 6/461; A61B 6/467; A61B 6/501; A61B 6/503; A61B 6/504; A61B 6/5217
See application file for complete search history.

(56) References Cited

U.S. PATENT DOCUMENTS

| | | | |
|---|---|---|---|
| 6,501,848 B1 | 12/2002 | Carroll et al. | |
| 6,792,302 B2 | 9/2004 | Wintermark et al. | |
| 8,588,491 B2 * | 11/2013 | Ikeda | A61B 6/032 382/131 |

(Continued)

OTHER PUBLICATIONS

Konig et al., Diagnosis of Cerebral Infarction Using Perfusion CT: State of the Art, Siemens, 2000, pp. 9-12, electromedica 68.

(Continued)

*Primary Examiner* — Michael Rozanski (57) ABSTRACT

A perfusion analysis system includes a perfusion modeller and a user interface. The perfusion modeller generates a patient specific perfusion model based on medical imaging perfusion data for the patient, a general perfusion model, and a quantification of one or more identified pathologies of the patient that affect perfusion in the patient. The user interface accepts an input indicative of a modification to the quantification of the one or more identified pathologies. In response, the perfusion modeller updates the patient specific perfusion model based on the medical imaging perfusion data for the patient, the general perfusion model, and the quantification of the one or more identified pathologies of the patient, including the modification thereto.

19 Claims, 5 Drawing Sheets

(56) References Cited

U.S. PATENT DOCUMENTS

| | | | | |
|---|---|---|---|---|
| 8,781,193 | B2* | 7/2014 | Steinberg | G06T 7/0022 600/481 |
| 9,144,394 | B2* | 9/2015 | Cohen | A61B 5/7425 600/424 |
| 9,173,590 | B2* | 11/2015 | Moats | G06T 7/0012 |
| 9,324,143 | B2* | 4/2016 | Goyal | A61B 6/507 |
| 2005/0283070 | A1 | 12/2005 | Imielinska et al. | |
| 2012/0184843 | A1* | 7/2012 | Kao | A61B 5/0042 600/419 |
| 2014/0364720 | A1* | 12/2014 | Darrow | A61B 5/748 600/410 |

OTHER PUBLICATIONS

Ezzeddine et al., CT Angiography With Whole Brain Perfused Blood Volume Imaging, Stroke, Apr. 2002, pp. 959-966. http://www.strokeaha.org.

Teksam et al., CT perfusion imaging in the early diagnosis of acute stroke, Diagnostic and Interventional Radiology, Dec. 2005, pp. 202-205, vol. 11, issue 4.

Martin Wiesmann, The basics of the method and interpreting images CT Perfusion of the Brain, Visions Computed Tomography, 2006, pp. 6-8, vol. 9.

Wintermerk et al., Perfusion—CT Assessment of Infarct Core and Penumbra: Receiver Operating Characteristic Curve Analysis in 130 Patients Suspected of Acute Hemispheric Stroke, Stroke Journal of the American Heart Association, Apr. 2006, pp. 979-985, http://stroke.ahajournals.org/cgi/content/full/37/979.

Busch, S., et al.; Visual and automatic grading of coronary artery stenoses with 64-slice CT angiography in reference to invasive angiography; 2006; European Radiology; 17(6)1445-1451.

Miles, K. A., et al.; Perfusion CT: a worthwhile enhancement?; 2003; British Journal of Radiology; 76:220-231.

Tomandl, B. F., et al.; Comprehensive Imaging of Ischemic Stroke with Multisection CT; 2003; Radiographics; 23(3) 565-592.

* cited by examiner

PERFUSION IMAGING SYSTEM WITH A PATIENT SPECIFIC PERFUSION MODEL

CROSS REFERENCE TO RELATED APPLICATIONS

This application is a Continuation-in-Part of U.S. Ser. No. 12/920,483 filed Sep. 1, 2010, which was a national filing of PCT application Serial No. PCT/IB2009/050757, filed Feb. 25, 2009, published as WO 2009/115935 A1 on Sep. 24, 2009, which claims the benefit of U.S. provisional application Ser. No. 61/037,010 filed Mar. 17, 2008, which is incorporated herein by reference.

The following generally relates to perfusion imaging, and finds particular application to computed tomography perfusion (CTP). However, it also amenable to other medical imaging applications and to non-medical imaging applications.

Computed tomography perfusion (CTP) is a medical imaging technique that is used to facilitate diagnosing patients with mal-perfusion of the brain like stroke patients. In general, the procedure begins with administering an intravenous contrast agent bolus to a patient. Then, the patient's brain is scanned. The contrast agent causes the x-ray density of the brain to temporarily increase as the contrast agent flows through the vascular structure of the brain. The imaging technique includes acquiring data that covers multiple different time intervals so that the contrast agent is captured and traced as the contrast agent flows through the vascular structure of the brain. The resulting image data can be used identify ischemic tissue and/or differentiate between irreversibly damaged tissue (necrotic tissue, or the core of the infarct) and potentially reversibly damaged tissue (at-risk tissue, or the penumbra of the infarct), for example, in stroke patients.

Figure 5:
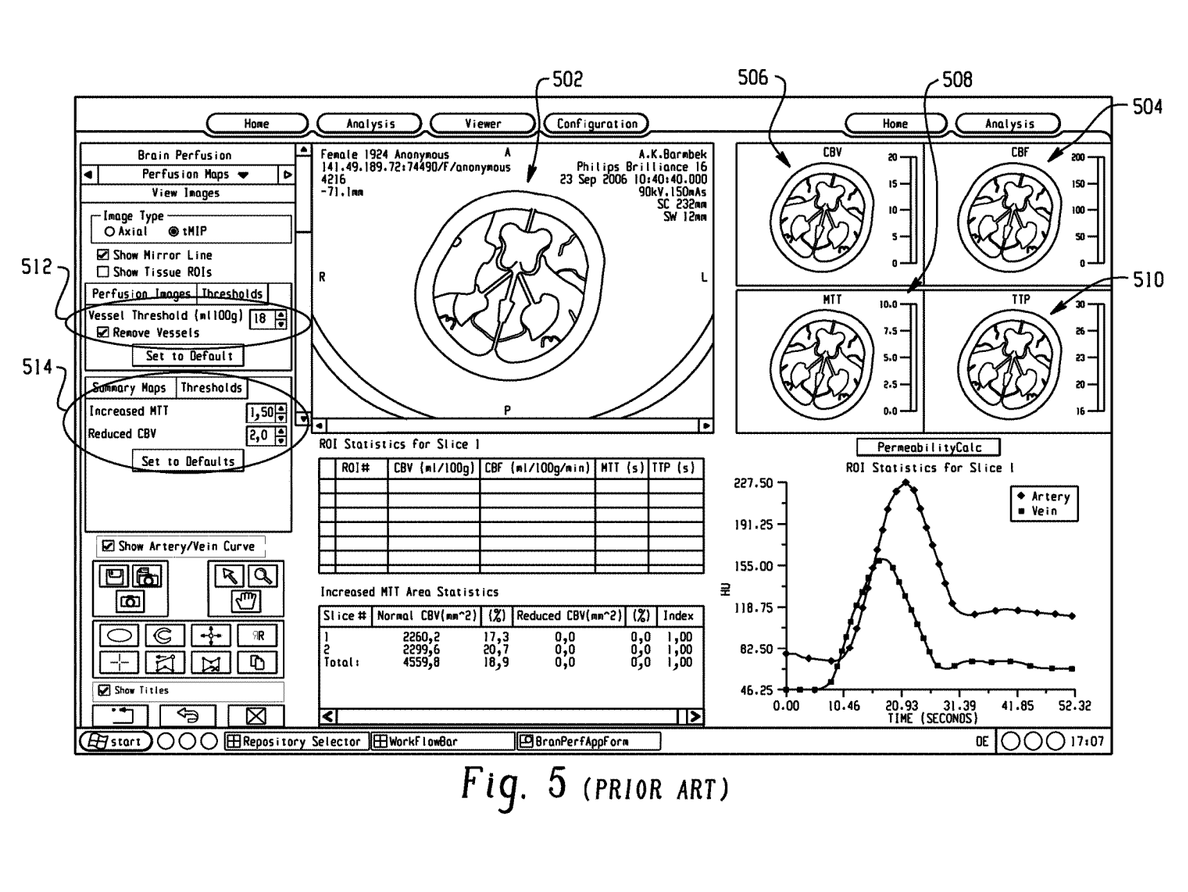
FIG. 5 illustrates a prior art perfusion technique.

Software application brain perfusion packages provide tools that facilitate automatically or semi-automatically interpreting CTP image data. Such packages may not only calculate perfusion maps showing cerebral blood flow (CBF), cerebral blood volume (CBV), mean transit time (MTT), and time to peak (TTP), but, in addition, may facilitate interpreting these perfusion maps by generating summary maps in which areas of hypo-perfusion are differentiated in the core of an infarct and the penumbra of the infarct. This differentiation may impact the therapeutic decision making, for example, where the quotient of the area of the core and the penumbra is used to decide whether thrombolytic therapy should be applied in an attempt to save potentially reversibly damaged tissue. For illustrative purposes, FIG. 5 shows a graphical user interface of an example software application brain perfusion package. In this example, a summary map 502, a CBF perfusion map 504, a CBV perfusion map 506, a MTT perfusion map 508, and a TTP perfusion map 510 are presented in the graphical user interface.

However, cerebral perfusion and diffusion deficits cannot be interpreted as a disease of the brain alone; they typically are treated and interpreted as a systemic disease, which may be caused by different malfunctions or malformations of the vascular system. Unfortunately, some contemporary software application brain perfusion packages may rely on brain perfusion image data alone. This can lead to a misinterpretation, for example, in cases where the perfusion deficit is apparent in the image data of the brain, but located outside the brain. For example, a stenosis of a carotid may mimic a mal-perfusion such as a hypo-perfusion of the corresponding cerebral hemisphere. Thus, additional information about the status of the extra-cranial vascular system should be used to allow for a more reliable interpretation of a CTP study of the brain.

Conventionally, a clinician such as a radiologist or the like interprets the perfusion map and/or the summary maps derived from the CTP image data and interprets the additional information, and mentally pieces the interpretations together and/or manually tweaks the parameters of the perfusion and/or summary maps based on the interpretation of the additional information. The later is shown in FIG. 5 in which the user manually adjusts a perfusion map parameter 512 and/or summary map parameters 514 via the graphical user interface. Unfortunately, determining such parameters can be tedious, time-consuming and prone to error. By way of example, where the additional information includes angiographic studies such as CT angiographies (CTA) that cover the body from the head to the heart, the clinician interprets the angiographic studies and then combines the image based findings (CTP and CTA) with clinical symptoms, for example, by determining suitable perfusion parameters based on the CTA findings and then adjusting the parameters 512 and 514 in the graphical user interface accordingly.

Furthermore, if new additional information becomes available or if any of the additional information changes, the clinician has to interpret the new or changed information and again mentally combine the findings and set the parameters 512 and 514 accordingly. As a consequence, although the additional information allows for a more reliable interpretation of a CTP study, it requires further interpretation of additional information outside of the CTP image data to generate parameters used to compensate or adjust for the shortcomings of the CTP analysis.

Aspects of the present application address the above-referenced matters and others.

According to one aspect, a perfusion analysis system includes a perfusion modeller and a user interface. The perfusion modeller generates a patient specific perfusion model based on medical imaging perfusion data for the patient, a general perfusion model, and a quantification of one or more identified pathologies of the patient that affect perfusion in the patient. The user interface accepts an input indicative of a modification to the quantification of the one or more identified pathologies. In response, the perfusion modeller updates the patient specific perfusion model based on the medical imaging perfusion data for the patient, the general perfusion model, and the quantification of the one or more identified pathologies of the patient, including the modification thereto.

According to another aspect, a brain perfusion analysis method includes identifying a first pathology of the vascular system, quantifying the first pathology, and generating a first patient specific brain perfusion model based on the quantification of the first pathology, a general brain perfusion model, and brain perfusion imaging data.

According to another aspect, a computer readable storage medium containing instructions which, when executed by a computer, cause the computer to perform the steps of: identifying a pathology of the vascular system; quantifying the pathology; and generating a patient specific brain perfusion model based on a quantification of the pathology, a general brain perfusion model, and a perfusion imaging data.

The invention may take form in various components and arrangements of components, and in various steps and arrangements of steps. The drawings are only for purposes of illustrating the preferred embodiments and are not to be construed as limiting the invention.

Figure 1:
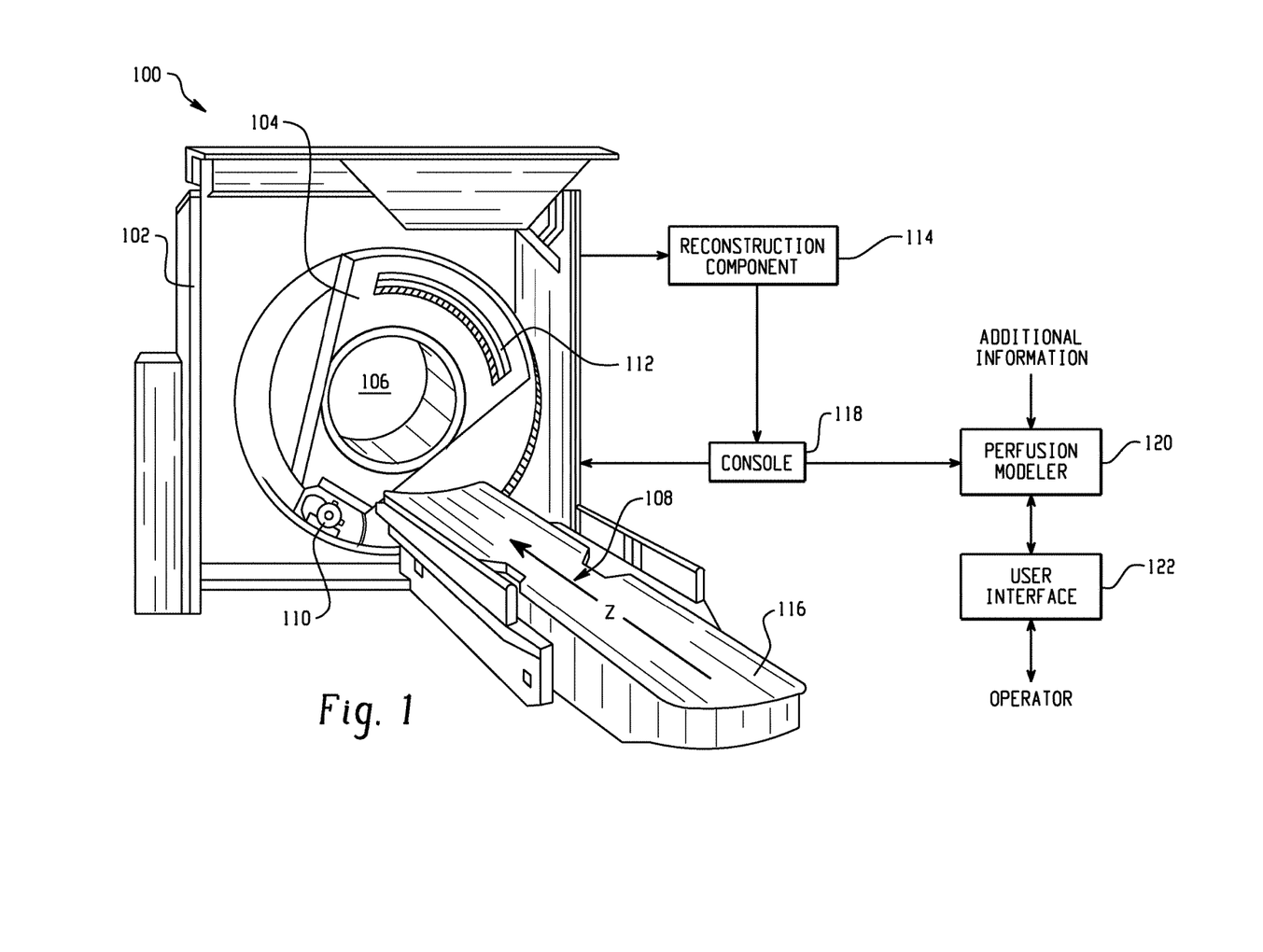
FIG. 1 illustrates a medical imaging system, including a perfusion modeller.

Initially referring to FIG. 1, a computed tomography (CT) scanner 100 includes a stationary gantry 102, which is stationary in the sense that it is generally stationary during scanning. However, the stationary gantry 102 may be configured to tilt and/or otherwise be moved.

The scanner 100 also includes a rotating gantry 104, which is rotatably supported by the stationary gantry 102. The rotating gantry 104 rotates around an examination region 106 about a longitudinal or z-axis 108.

A radiation source 110, such as an x-ray tube, is supported by and rotates with the rotating gantry 104 around the examination region 106. A fourth generation system is also contemplated. The radiation source 110 emits generally fan, wedge, or cone shaped radiation that traverses the examination region 106.

A radiation sensitive detector array 112 detects photons emitted by the radiation source 110 that traverse the examination region 106 and generates projection data indicative of the detected radiation. The illustrated radiation sensitive detector array 112 includes one or more rows of radiation sensitive photosensors that extend in a z-axis or longitudinal direction, and one or more columns of radiation sensitive photo sensors that extend in a traverse direction.

A reconstructor 114 reconstructs the projection data from the detectors to generate volumetric image data indicative of the examination region 106, including the interior anatomy, such as a portion of the vascular system, of a patient disposed in the examination region 106.

A patient support 116, such as a couch, supports a patient in the examination region 106. The patient support 116 is movable along the z-axis 108 in coordination with the rotation of the rotating gantry 104 to facilitate helical, axial, or other desired scanning trajectories.

A general purpose computing system 118 serves as an operator console, which includes human readable output devices such as a display and/or printer and input devices such as a keyboard and/or mouse. Software resident on the console 118 allows the operator to control the operation of the system 100, for example, by allowing the operator to select or define a scan protocol, initiate and terminate scanning, view and/or manipulate the volumetric image data, and/or otherwise interact with the system 100.

In one instance, the scanner 100 is used to perform a cerebral perfusion scan. Such a scan may include administering an intravenous contrast medium bolus, such as an iodinated contrast agent, to a subject, and then scanning the subject's brain over time. Following the administration of the contrast medium bolus, the x-ray density of the brain temporarily changes as the contrast medium flows through the vascular structure of the brain, and the quantity of the contrast material is captured and tracked as it passes through the vascular structure of the brain. As noted above, the resulting image data can be used identify ischemic tissue and/or differentiate between irreversibly damaged tissue and potentially reversibly damaged tissue, for example, in stroke patients or patients with another neuro-vascular disease. Of course, the scanner 100 can additionally or alternatively be used for other CT applications.

When performing such a cerebral perfusion scan, the resulting image data can be transferred to a perfusion modeller 120. In this example, the perfusion modeller 120 is part of a workstation or the like, which is separate from the scanner 100. However, the perfusion modeller 120 can additionally or alternatively be implemented in the console 118 and/or be part of another system. The perfusion modeller 120 generates patient specific cerebral perfusion information at least in part from the image data. In one instance, the patient specific cerebral perfusion information is an adaptation of a general cerebral perfusion model. The general model may include an equation or the like in terms of various perfusion related parameters, be based on one or more rules, etc. Such a general model may be modified to include and/or remove a parameter(s), change a dependency (s), and/or otherwise be modified.

In one instance, the patient specific perfusion model includes information indicative of parameters such as cerebral blood flow (CBF), cerebral blood volume (CBV), mean transit time (MTT), time to peak (TTP), and/or one more other parameters, and/or summary information. As shown, the illustrated perfusion modeller 120 also uses other or additional information to generate the patient specific cerebral perfusion model. As described in greater detail below, the additional information may include image data from other scans and/or information derived therefrom, physiological parameters (e.g., vital signs), patient history, patient pathologies such as vascular pathologies, etc.

A user interface 122 provides a mechanism through with an operator and the perfusion modeller 120 interact with each other. Such interaction may include presenting, via the user interface 122, various information such as individual and/or superimposed images from one or more imaging procedures. For example, the user interface 122 may present CT data, CTP data, CTA data, data from other imaging modalities, and/or a combination (via overlays or superposition) thereof as two- or three-dimensional image data and/or other image data and/or as time sequences of the before mentioned data. The user interface 122 may additionally or alternatively present pathologies within the images, the perfusion maps (e.g., CBF, CBV, MTT and/or TTP maps), summary maps, statistics, parameter settings, etc. Such interaction may also include operator input such as additions, modifications, and/or deletions to the information provided to and used by the perfusion modeller 120 to generate the patient specific cerebral perfusion model.

It is to be appreciated that the perfusion modeller 120 dynamically updates or generates the patient specific cerebral perfusion model as its inputs change, for example, as parameters are added, modified, and/or removed. For example, a clinician may discover a pathology (e.g., a stenosis) in a CTA image that was not previously identified as a pathology. The clinician, via the user interface 122, may mark or otherwise identify the pathology to the perfusion modeller 120. In response, the perfusion modeller 120 updates or generates a patient specific perfusion model based on a combination of the CTP image data and the additional information, which now also includes the newly identified pathology. In instances in which such additional information is not used by the perfusion modeller 120, the clinician may be tasked with interpreting the additional information (e.g., other images, physiological parameters, etc.) and mentally drawing conclusions based on both the CTP findings (e.g., the perfusion maps showing CBF, CBV, MTT and ITT, and the summary map) and the findings from the additional information, and/or determining various parameters from the findings from the additional information and using the findings to determine parameters used to compensate for shortcomings in the CTP findings.

Figure 2:
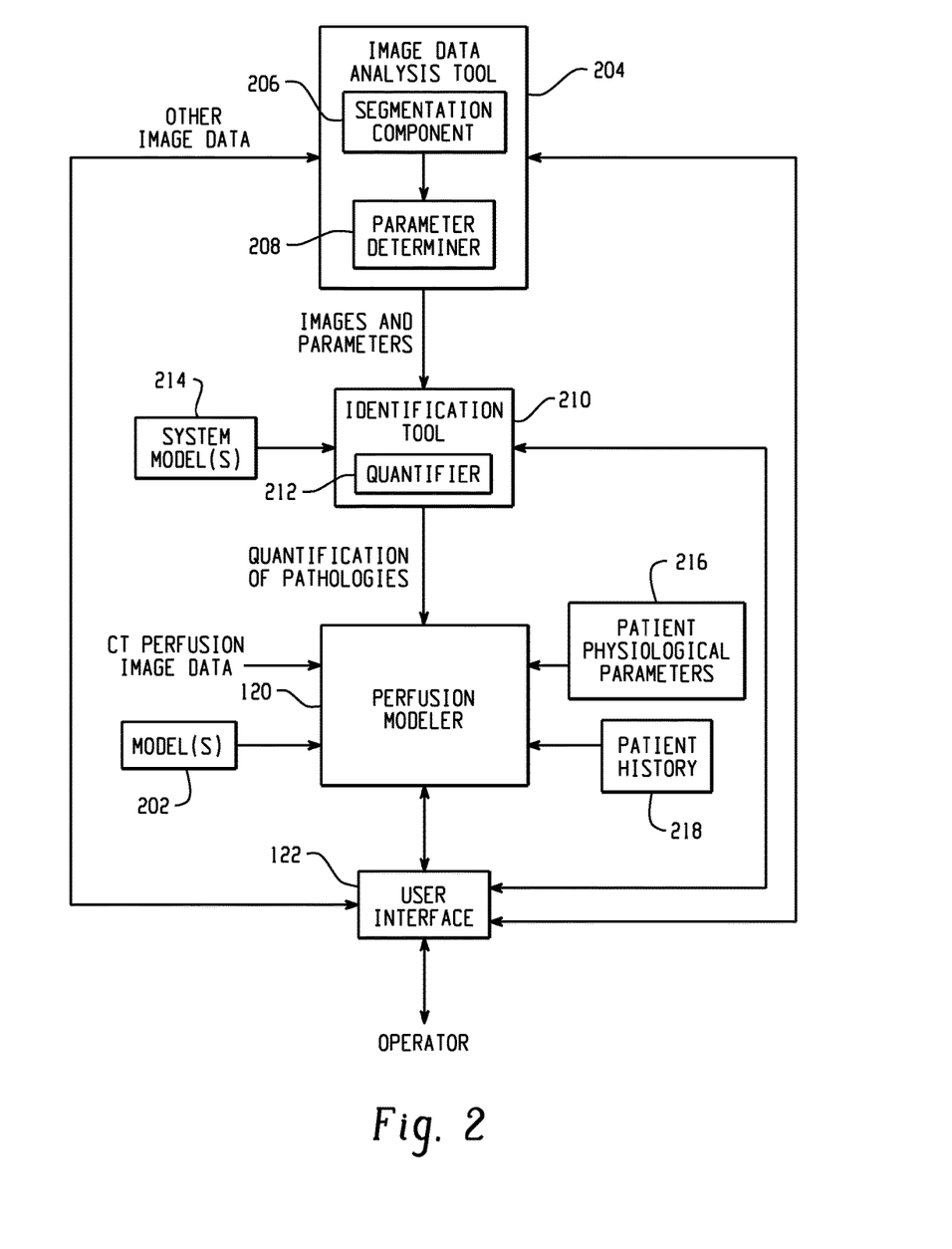
FIG. 2 illustrates example inputs to the perfusion modeller.

FIG. 2 illustrates a non-limiting example showing various types of inputs that may be used by the perfusion modeller 120 to generate the patient specific cerebral perfusion model. As discussed above, one of the inputs is the CT perfusion image data acquired by the scanner 100. Another input includes a general cerebral perfusion model 202. Such a model may be based on parameters such as systemic parameters like blood pressure, cardiac parameters like heart rate, vascular parameters like the perimeter of the carotids, changes in cerebral perfusion parameters caused by pathological inputs, and/or other parameters. Examples of suitable cerebral perfusion parameters include, but are not limited to, parameters indicative of a cerebral mal-perfusion, delayed means transit time cause by low blood pressure, etc. It is to be appreciated that the parameters and/or dependencies of the model can be changed, including tailored for a particular patient, pathology, and/or clinician. In this example, the CT perfusion image data, the general cerebral perfusion model 202, and one or more of the following additional information is used by the perfusion modeller 120 to generate a patient specific cerebral perfusion model.

In one instance, the additional information includes pathological information such as a quantification of pathologies and/or pathological information. In one example, the quantification of a pathology is determined from image data. Such image data may be CT data, including CT angiography (CTA) data, CTP data, and/or other CT data, from the scanner 100 or another CT scanner, and/or image data from different imaging modalities, including magnetic resonance (MR), ultrasound (US), single photon emission computed tomography (SPECT), positron emission tomography (PET), etc. The image data is processed by an image data analysis tool 204.

A segmentation component 206 segments the image data, for example, to extract one or more regions of interest (ROI) and/or discard one or more regions outside of the one or more ROI's. This can be done automatically and/or with human intervention. In one example, the segmented data includes information indicative of vascular structures. For instance, the segmentation component 206 can segment CTA images or the like to obtain vascular structures such as a vascular tree. A parameter determiner 208 of the image data analysis tool 204 determines various vascular parameters from the segmented vascular structures. Examples of such parameters include parameters indicative of the perimeter of the carotids, cerebral mal-perfusion (e.g., hypo-perfusion caused by stenosis), delayed means transit time cause by low blood pressure, etc.

An identification tool 210 identifies and quantifies pathologies in the vascular structure based on the segmented data and the parameters derived therefrom by the image data analysis tool 204. In one instance, a quantifier 212 of the identification tool 210 compares the image data of the segmented vascular structures with one or more models 214 including image data with vascular structure with known pathologies to identify pathologies. In another instance, a machine learning technique, such as through an implicitly and/or explicitly trained classifier, probabilities, cost functions, statistics, heuristics, or the like are used to identify vascular pathologies. The quantification of the identified pathologies are provide to the perfusion modeller 120.

The additional information may also include patient physiological parameters 216. Such parameters may include, and are not limited to, blood pressure, heart rate, and the like. In one instance, these parameters are measured and provided by an operator. In another instance, these parameters may additionally or alternatively be provided by an external information source such as a Radiology Information Source (RIS), a Picture Archiving and Communication System (PACS), and/or other medical information storage, retrieval and distribution system. In another instance, these parameters may additionally or alternatively be derived from image data such as CTA image data. The additional information may additionally include patient medical history.

The illustrated perfusion modeller 120 uses the above discussed input to generate the patient specific perfusion model. As such, the patient specific cerebral perfusion model is based on the CTP image data, the general perfusion model, and the additional information. The patient specific cerebral perfusion model may include information indicative of CBF, CBV, MTT, TTP, and/or one more other parameters. As discussed above, such information along with various image data is presented to the operator via the user interface 122, and an operator can add, modify, and/or delete various inputs to the perfusion modeller 120 via the user interface 122. Upon any changes by the operator, the perfusion modeller 120 generates an updated or new patient specific perfusion model based on the CTP image data and the general perfusion model and the additional information with any changes made thereto.

Although the perfusion image data in the above examples is acquired by the CT scanner 100, it is to be appreciated that perfusion image data can additionally or alternatively be acquired by another imaging modality such as MR, US, SPECT, PET, etc.

Operation is now described in connection with FIG. 3.

At 302, a general cerebral perfusion model is obtained. This model may be based on systematic, cardiac, vascular structure, and/or other parameters.

At 304, image data indicative of pathologies of the vascular system and/or of cerebral mal-perfusion is obtained. Such data may be acquired by the CT scanner and/or another type of scanner.

At 306, vascular pathologies are identified and quantified. Briefly turning to FIG. 4, an example of this is illustrated. At 402 a set of CTA (and/or MRA and/or DSA) images of the heart and brain are obtained. At 404, the set of images is segmented to generate a vessel tree structure. At 406, a pathology in the vessel tree structure is detected using a generic model of the vascular structure. At 408, the pathology is quantified.

Returning to FIG. 3, at 308 patient specific physiological parameters are obtained. Such parameters include, but are not limited to, the systemic parameters, the cardiac parameters, the vascular parameters, and/or the other parameters.

At 310, the perfusion modeller 120 determines a patient specific cerebral perfusion model based on a general perfusion model, the image data, the quantification of the identified pathologies, the patient specific parameters, and a patient history. Turning to FIG. 4, this is shown at 410.

Returning to FIG. 3, at 312, the patient specific perfusion model is presented to the operator via a user interface or the like.

At 314, the operator may modify or adjust the general perfusion model, the image data, the identified pathologies, the patient specific parameters, and/or the patient history. If the operator makes any modifications or adjustments, then at least act 310 is repeated, and a new patient specific cerebral perfusion model is presented at 312.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer. The acts need not be performed concurrently with data acquisition.

Figure 3:
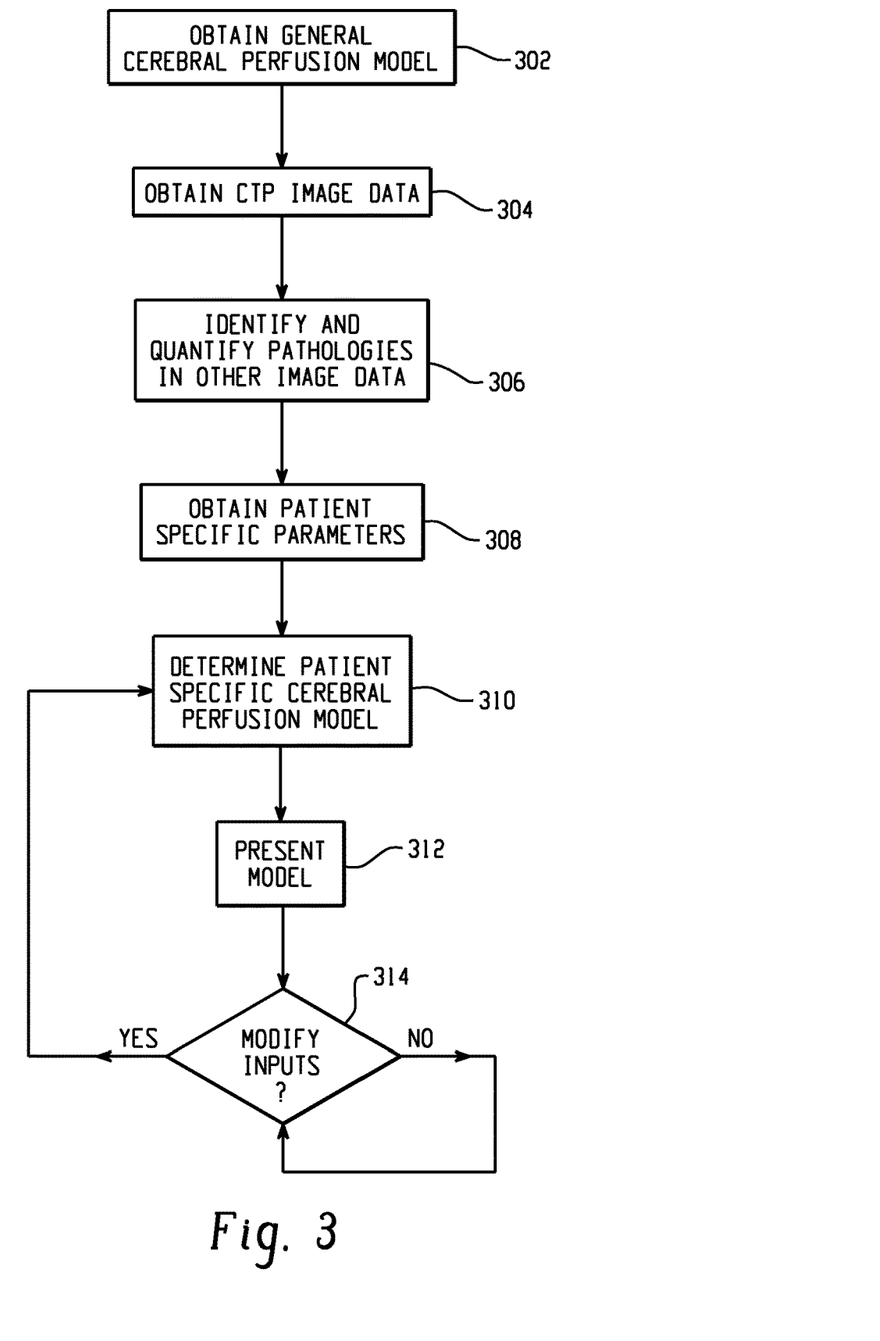
FIG. 3 illustrates a flow diagram for modeling perfusion.
Figure 4:
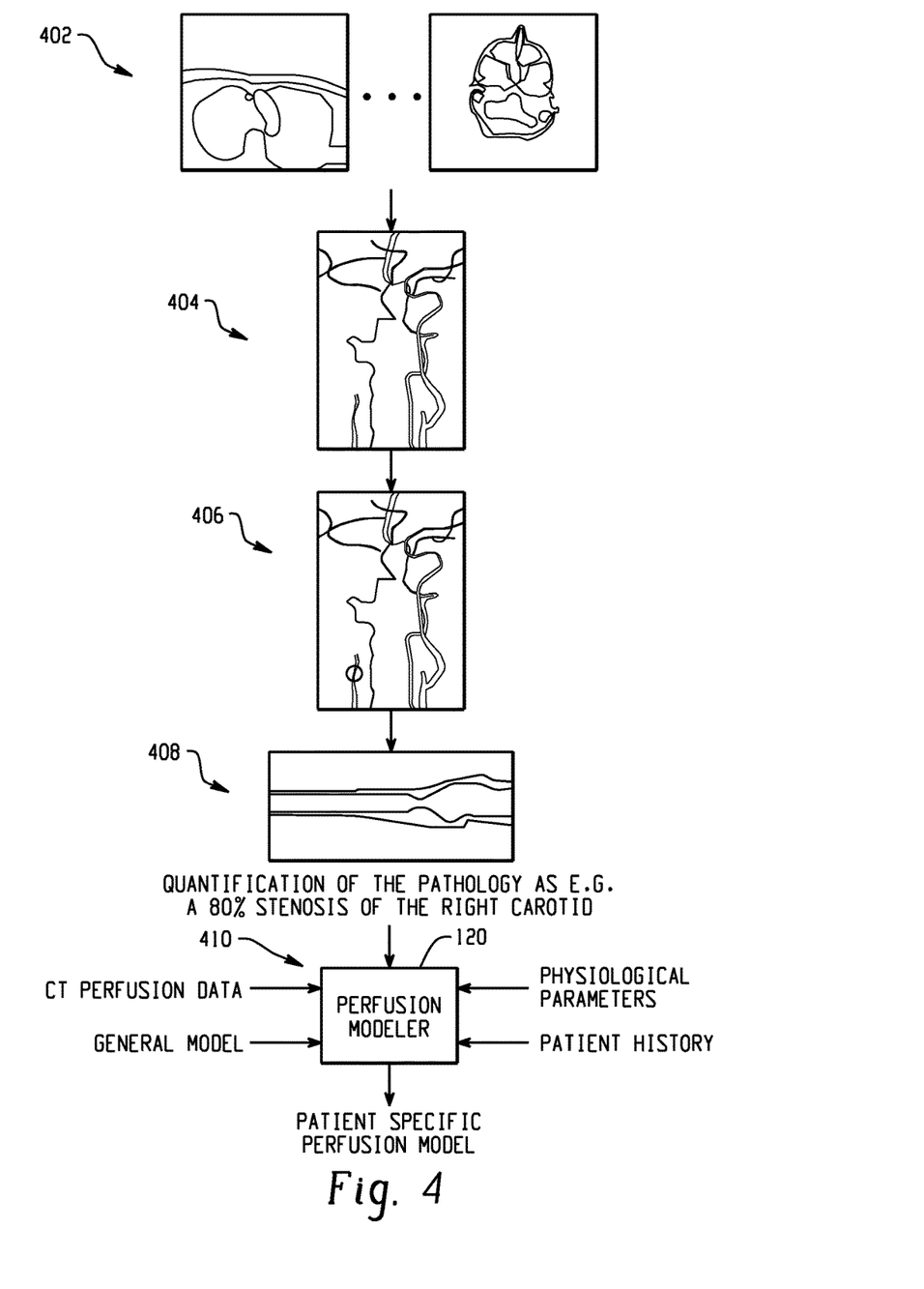
FIG. 4 illustrates a flow diagram for modeling perfusion.

The following illustrates a non-limiting example based on the method of FIG. 3.

Cerebral blood flow (CBF) is a perfusion parameter describing brain perfusion and brain perfusion deficits, which is indicative for e.g. stroke patients. The cerebral blood flow cannot be calculated directly, but can be derived by applying a general perfusion model. In accordance to such a model the cerebral blood flow (CBF) can be calculated from the cerebral blood volume (CBV) and the mean transition time (MTT). A general cerebral perfusion model for CBF is shown in EQUATION 1:

$$CBF = \frac{CBV}{MTT}. \quad \text{EQUATION 1}$$

These parameters can be calculated based on CTP images and the resulting time concentration curves for the artery $C_a(t)$, the vein $C_v(t)$ and the tissue $C_b(t)$. Different models are available that describe, how to calculate the physiological parameters based on the time concentration curve. Some of these models are compared by Wintermark et al., "Quantitative assessment of regional cerebral blood flows by perfusion CT studies at low injection rates: a critical review of underlying theoretical models," Eur. Radiol. 2001, Vol. 11, pp. 1220-1230.

In the above, the MTT is assumed to be measured from an ideal instantaneous bolus of contrast material. However, there is a variable delay between the time, the bolus is injected and the arrival of the bolus at the arteries supplying a given region of the brain. Furthermore, variable pathways in the lung will result in a prolonged bolus if the contrast agent in the tissue. Moreover, recirculation of contrast agent will prevent that the time concentration curve will ever fall to zero.

The delay and the prolongation of the bolus can be corrected by the arterial input function as described, for example, in Axel, "," Adv. Neurol. 1981, Vol. 30, pp. 67-71. However, several patient specific parameters will also influence the delay and prolongation of the bolus. An example includes systemic parameters and cardiac parameters e.g. blood pressure, heart rate, blood volume, geometry and elasticity of the blood vessels, etc. Another example includes pathologies e.g. of the vascular system like stenosis as for example measured by CTA imaging.

When a stenosis (of the carotid) is present, blood must reach the tissue in the distribution of the affected vessel via collateral pathways, which will often introduce additional delay in arrival of the contrast bolus. Based on CT Angiography (CTA) images, the stenosis of the carotid can be measured. In addition, the pathway of the collateral vessels, which will take over the supply of the tissue in the distribution of the (partially) blocked carotid, can be detected and its length can be measured.

The perfusion modeler 120, in one non-limiting instance, generates a patient specific cerebral perfusion model by modeling the total blood supply of the tissue in the distribution of the affected carotid $CBF_{total}$ as a summation of the reduced blood supply of affected carotid $CBF_{stenosis}$ and the blood supply due to the collateral vessels $CBF_{collateral}$. An example summation is shown in EQUATION 2:

$$CBF_{total} = CBF_{stenosis} + CBF_{collateral}. \quad \text{EQUATION 2}$$

The time concentration curve of the arterial blood flow $C_a(t)$, the venous blood flow $C_v(t)$, and the tissue $C_b(t)$ will be delayed and prolonged due to the blood supply by the collateral vessels. The delay and the prolongation are proportional to the degree of the stenosis and to the extension of the collateral pathway. Both the degree of the stenosis $d_{stenosis}$ and the extension of the arterial pathway $\Delta l$ can be calculated, for example, as shown in EQUATION 3:

$$C_a(t) = C_a(t)_{collateral} \times (1 - f(d_{stenosis})) + C_a(t - T_{\Delta 1})_{collateral} \times f(d_{stenosis}) \quad \text{EQUATION 3:}$$

$T_{\Delta 1}$ is a delay due to extended pathway, $C_a(t)_{collateral}$ it a time concentration curve of the contralateral (non-affected) carotid, and $f(d_{stenosis}) = \{x \in N | x \epsilon [0; 1]$, where $f(0)=0$ and $f(1)=1$. In one instance, it is assumed that the blood flow is equal for both carotids in the non-pathological cases. The influence of the degree of the stenosis and the extension of the arterial pathway can calculated by applying known and/or other fluid dynamic approaches.

It is to be understood that the above example is a non-limiting example provided only for explanatory purposes and sake of brevity. The perfusion modeler 120 can generate other patient specific cerebral perfusion models for CBF and/or other perfusion parameters. One of ordinary skill would understand, based on the description herein, how to make and use the perfusion modeler 120 without undue experimentation.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention claimed is:

1. A perfusion analysis system, comprising:
   a perfusion modeller that includes one or more processors configured to generate a patient specific perfusion model of a brain based on medical imaging perfusion data for a patient, a general perfusion model, and a quantification of one or more identified pathologies of the patient that affect perfusion in the brain of the patient; a user interface that accepts an input, wherein the general model is based on a vascular structure parameter; and
   an image analysis tool that includes the one or more processors configured to determine the vascular structure parameter, wherein the image analysis tool includes:
   a segmentation component that includes the one or more processors configured to segment image data to obtain mace data indicative of corresponding vascular structure; and
   a parameter determiner that includes the one or more processors configured to determine the vascular structure parameter based on the segmented image data.

2. The system of claim 1, wherein the one or more identified pathologies of the patient that affect perfusion in the patient includes a pathology of a vascular structure that supplies blood flow to the brain, wherein the perfusion modeller changes parameters of the patient specific perfusion model of the brain based on the quantification of the pathology of the vascular structure that supplies blood flow to the brain.

3. The system of claim 2, wherein a pathology of the vascular structure that supplies blood flow to the brain includes a stenosis, wherein the perfusion modeller changes the patient specific perfusion model according to blood flow of the vascular structure with the stenosis and collateral blood flow.

4. The system of claim 1, wherein the patient specific model includes a delayed mean transit time parameter changes according to a change in a value of at least one from a group comprising of a blood pressure of the patient, a heart rate of the patient, a blood volume, a geometry of the vascular structure, an elasticity of a vessel in the vascular structure.

5. The system of claim 1, further including:
an identification tool that includes the one or more processors configured to identify and quantify a pathology based on the segmented image data and the vascular structure parameter.

6. The system of claim 5, wherein the identification tool includes:
a quantifier that includes the one or more processors configured to compare the segmented image data with a vascular system model to identify the pathology.

7. The system of claim 1, wherein the perfusion modeller generates the patient specific perfusion model based on one or more patient physiological parameters including at least one of blood pressure or heart rate.

8. The system of claim 1, wherein the perfusion modeller generates the patient specific perfusion model based on a patient medical history of the patient.

9. The system of claim 1, wherein the patient specific perfusion model includes at least one of a cerebral blood flow map, a cerebral blood volume map, a mean transit time map, or a time to peak map.

10. The system of claim 1, wherein the medical imaging perfusion data includes computed tomography data generated by a computed tomography scanner.

11. A brain perfusion analysis method, comprising:
identifying, with a processor, a first pathology of the vascular system;
quantifying, with the processor, the first pathology;
generating, with the processor, a first patient specific brain perfusion model based on the quantification of the first pathology, a general brain perfusion model, and brain perfusion imaging data;
segmenting, with the processor, image data to obtain a vascular tree structure; and
determining, with the processor, a vascular parameter of the vascular tree structure, wherein the first pathology is identified and quantified in the vascular tree structure based on the vascular parameter.

12. The brain perfusion analysis method of claim 11, further including:
identifying a second pathology of the vascular system;
quantifying the second pathology; and
generating a second patient specific brain perfusion model based on the quantification of the first pathology, the quantification of the second pathology, the general brain perfusion model, and the perfusion imaging data.

13. The brain perfusion analysis method of claim 12, wherein the first pathology includes a stenosis of an artery that supplies blood flow to the brain, wherein the second pathology includes low blood pressure.

14. The brain perfusion analysis method of claim 11, wherein the identification of the first pathology includes comparing image data indicative of at least a sub-portion of the vascular system with a vascular system model including known pathologies.

15. A non-transitory computer readable storage medium containing instructions which, when executed by a computer, cause the computer to:
identify a pathology of the vascular system that supplies blood to the brain;
quantify the pathology;
generate a patient specific brain perfusion model based on a quantification of the pathology, a general brain perfusion model, and perfusion imaging data;
segment image data to obtain a vascular tree structure; and
determine a vascular parameter of the vascular tree structure, wherein the pathology is identified and quantified in the vascular tree structure based on the vascular parameter.

16. The non-transitory computer readable storage medium of claim 15, wherein the instructions, when executed by the computer, further cause the computer to:
present the patient specific brain perfusion model in a human readable format in a user interface;
accept a modification of the identified pathology through the user interface.

17. The non-transitory computer readable storage medium of claim 15, wherein the instructions, when executed by the computer, further cause the computer to:
present the patient specific brain perfusion model in a human readable format in a user interface;
accept a second pathology through the user interface.

18. The non-transitory computer readable storage medium of claim 17, wherein the instructions, when executed by the computer, further cause the computer to:
generate a second patient specific brain perfusion model based on the quantification of the pathology, a quantification of the second pathology, the general brain perfusion model, and the perfusion imaging data.

19. The non-transitory computer readable storage medium of claim 15, wherein the instructions, when executed by the computer, further cause the computer to:
generate the patient specific brain perfusion model based on patient vital signs and patient medical history.

* * * * *